United States Patent
Frost et al.

(10) Patent No.: US 8,564,303 B2
(45) Date of Patent: Oct. 22, 2013

(54) SYSTEMS AND METHODS FOR DETECTING ANOMALIES IN ELONGATE MEMBERS USING ELECTROMAGNETIC BACK SCATTER

(75) Inventors: Charles A. Frost, Albuquerque, NM (US); Ronald J Focia, Edgewood, NM (US)

(73) Assignee: WaveTrue, Inc., New York, NY (US)

( * ) Notice: Subject to any disclaimer, the term of this patent is extended or adjusted under 35 U.S.C. 154(b) by 340 days.

(21) Appl. No.: 12/652,975

(22) Filed: Jan. 6, 2010

(65) Prior Publication Data

US 2010/0171483 A1 Jul. 8, 2010

Related U.S. Application Data

(60) Provisional application No. 61/142,843, filed on Jan. 6, 2009.

(51) Int. Cl.
- *G01R 31/08* (2006.01)
- *G01R 31/28* (2006.01)
- *G01R 31/11* (2006.01)

(52) U.S. Cl.
USPC ............ 324/536; 324/529; 324/530; 324/533

(58) Field of Classification Search
USPC .................. 324/529, 530, 533, 536
See application file for complete search history.

(56) References Cited

U.S. PATENT DOCUMENTS

| | | | |
|---|---|---|---|
| 2,698,923 A | 1/1955 | Edson | |
| 2,849,683 A | 8/1958 | Miller | |
| 3,079,552 A | 2/1963 | Walker | |
| 4,523,473 A | 6/1985 | Chamuel | |
| 4,932,810 A | 6/1990 | Austin | |
| 4,970,467 A | 11/1990 | Burnett | |
| 5,189,374 A | 2/1993 | Burnett | |
| 5,243,294 A | 9/1993 | Burnett | |
| 5,270,661 A | 12/1993 | Burnett | |
| 5,719,503 A | 2/1998 | Burnett | |
| 5,747,998 A | 5/1998 | Fowler | |
| 5,933,012 A * | 8/1999 | Bengtsson et al. | 324/524 |
| 5,942,687 A | 8/1999 | Simmonds et al. | |
| 6,005,396 A * | 12/1999 | Suyama et al. | 324/639 |
| 6,020,733 A | 2/2000 | Bradley | |
| 6,065,348 A | 5/2000 | Burnett | |
| 6,072,316 A | 6/2000 | Burnett | |
| 6,078,280 A | 6/2000 | Perdue et al. | |
| 6,157,183 A | 12/2000 | Bradley | |
| 6,194,902 B1 | 2/2001 | Kuo et al. | |

(Continued)

OTHER PUBLICATIONS

International Searching Authority, PCT International Search Report, May 6, 2010, 3 pages.

(Continued)

*Primary Examiner* — Amy He

(74) *Attorney, Agent, or Firm* — Michael R. Schacht; Schacht Law Office, Inc.

(57) ABSTRACT

An anomaly on an elongate conductive member is detected by causing a source electromagnetic wave to propagate in a first direction along the elongate conductive member such that the source electromagnetic wave passes through the at least one anomaly. The anomaly causes a reflected electromagnetic wave to propagate in a second direction along the elongate conductive member. The second direction is opposite the first direction. The electric field of the reflected electromagnetic wave is sensed. The magnetic field of the reflected electromagnetic wave is sensed. A direction of propagation of the reflected electromagnetic wave is determined based on the electric field of the reflected electromagnetic wave and the magnetic field of the reflected electromagnetic wave.

11 Claims, 1 Drawing Sheet

(56) References Cited

U.S. PATENT DOCUMENTS

| | | | |
|---|---|---|---|
| 6,271,670 | B1 | 8/2001 | Caffey |
| 6,298,732 | B1 | 10/2001 | Burnett |
| 6,339,333 | B1 | 1/2002 | Kuo |
| 6,472,883 | B1 | 10/2002 | Burnett |
| 6,833,537 | B2 | 12/2004 | Risman et al. |
| 6,934,655 | B2 | 8/2005 | Jones et al. |
| 7,196,529 | B2 | 3/2007 | Burnett et al. |
| 7,642,790 | B2 | 1/2010 | Burnett et al. |
| 7,940,061 | B2 | 5/2011 | Focia et al. |
| 2005/0007121 | A1 | 1/2005 | Burnett et al. |
| 2005/0072236 | A1 | 4/2005 | Heyman |
| 2006/0145704 | A1 | 7/2006 | Burnett |
| 2008/0143344 | A1 | 6/2008 | Focia |
| 2008/0191706 | A1 | 8/2008 | Burnett et al. |
| 2008/0246485 | A1* | 10/2008 | Hibbs et al. ............... 324/332 |
| 2008/0265807 | A1* | 10/2008 | Rose .......................... 318/135 |
| 2008/0308567 | A1 | 12/2008 | Counts-Bradley |

OTHER PUBLICATIONS

Kroyer et al., "Operational Experience with the LHC Waveguide Mode Reflectometer", LHC Project Report 907 presented at EPAC, Jun. 2006, 4 pages.

Kroyer, "A Waveguide High Order Mode Reflectometer for the Large Hadron Collider Beam-pipe", CERN-AB-2003-085 RF, Sep. 2003, 76 pages.

Kroyer et al., "Reflectometer Application for the LHC Installation", LTC, Jun. 2006, 14 pages.

Kroyer, "Application of Waveguide Mode Diagnostics for Remote Sensing in Accelerator Beam Pipes", CERN, Dissertation, Aug. 2005, 135 pages.

Kroyer et al., "The LHC Beam Pipe Waveguide Mode Reflectometer", IEEE, 2007, 3 pages.

Caspers et al., "Waveguide Mode Reflectometry for Obstacle Detection in the LHC Beam Pipe Including Signal Attenuation", IEEE, 2003, 3 pages.

Caspers, "Coupler Structures for the LHC Beam Pipe Waveguide Mode Reflectometer", LHC Project Report 764 presented at EPAC, Jul. 2004, 4 pages.

Kroyer, "Coupler Structures for the LHC Beam Pipe Waveguide Mode Reflectometer", LHC Project Report 764, presented at EPAC, Jul. 2004, 4 pages.

Schmitz et al., German magazine "Nachrichten Elektronik + Telematik", vol. 37, No. 3, Mar. 1983, 7 pages.

Pramanick et al., "Handbook of Microwave Technology", vol. 1, 1995, 4 pages.

* cited by examiner

SYSTEMS AND METHODS FOR DETECTING ANOMALIES IN ELONGATE MEMBERS USING ELECTROMAGNETIC BACK SCATTER

RELATED APPLICATIONS

This U.S. patent application Ser. No. 12/652,975 filed Jan. 6, 2010, claims priority of U.S. Provisional Patent Application Ser. No. 61/142,843 filed Jan. 6, 2009.

TECHNICAL FIELD

The present invention relates to the detection of anomalies in elongate, conductive members and, more particularly, to the remote detection of anomalies in conductive members such as pipelines.

BACKGROUND

The present invention generally relates to the detection of anomalies in elongate conductive members. The present invention is of particular importance in the context of detecting anomalies such as corrosion in pipelines. Anomalies can affect the function of the elongate conductive member. As an example, corrosion of steel pipes can degrade the structural integrity of the pipeline system.

The present invention will be described in the context of detecting corrosion in a steel pipeline, but the present invention has broader application to any elongate member capable of conducting electromagnetic signals having an anomaly that affects propagation of such electromagnetic signals.

In some pipeline systems, the metallic pipe is insulated with a urethane foam covering and protected by an outer metallic shield. This is often done to prevent heat loss. In other cases, the metallic pipe may be buried under the ground. For insulated, shielded, and/or buried pipes, visual inspection for corrosion on the outside of a shielded steel pipe is virtually impossible without physically removing the insulation and outer shield and/or excavating the pipe. For these insulated shielded pipes, visual inspection is impossible without physically removing the insulation and outer shield.

Corrosion can also occur within a pipe. Visual inspection of the interior of the pipe is also very difficult and is not practically possible when the pipeline is in use. One currently used method for pipeline inspection is to pass an instrumented probe, called a pig, through the entire length of the pipe and read out recorded data from the pig. Many pipelines cannot be tested this way because their construction does not allow passage of the pig.

Other methods of inspecting pipes include acoustic wave propagation through the metal, eddy current measurements, and x-ray radiography, but these methods are only applicable to a single point measurement or over a short distance. All but x-ray radiography require direct access to the surface of the pipe.

The assignee of the present application is also the assignee of a number of patents and published patent applications that disclose systems and methods for remotely testing conductive elongate members such as pipes. The systems and methods disclosed in these patents and patent applications can effectively determine the distance from a given measurement point to one or more anomalies based on time delay between the initial exciting pulse and the reflection from the anomaly. In particular, the systems and methods disclosed in the cited patents and patent applications employed only electric field probes. Using only electric field probes or sensors to time the wave arrival of the incident and reflected pulses at a single probe location allows the distance to, but not the direction of, anomalies to be determined by wave propagation calculation. Accordingly, these systems and methods are generally not effective at determining the direction of an anomaly on the conductive member relative to the measurement point.

The need thus exists for improved systems and methods for nondestructively testing for anomalies within a pipe structure.

SUMMARY

The present invention may be embodied as a method of detecting an anomaly on an elongate conductive member comprising the following steps. A source electromagnetic wave is caused to propagate in a first direction along the elongate conductive member such that the source electromagnetic wave passes through the at least one anomaly. The anomaly causes a reflected electromagnetic wave to propagate in a second direction along the elongate conductive member. The second direction is opposite the first direction. The electric field of the reflected electromagnetic wave is sensed. The magnetic field of the reflected electromagnetic wave is sensed. A direction of propagation of the reflected electromagnetic wave is determined based on the electric field of the reflected electromagnetic wave and the magnetic field of the reflected electromagnetic wave.

The present invention may also be embodied as a system for detecting an anomaly on an elongate conductive member comprising a pulse generator, an electric field sensor, a magnetic field sensor, and a processor. The pulse generator causes first and second source electromagnetic waves to propagate in first and second directions, respectively, along the elongate conductive member such that one of the first and second source electromagnetic waves passes through the at least one anomaly. The anomaly causes a reflected electromagnetic wave to propagate along the elongate conductive member. The electric field sensor senses the electric field of the reflected electromagnetic wave. The magnetic field sensor senses the magnetic field of the reflected electromagnetic wave. The processor determines a direction of propagation of the reflected electromagnetic wave based on the electric field of the reflected electromagnetic wave and the magnetic field of the reflected electromagnetic wave.

The present invention can also be embodied as a method of determining whether anomalies are present on an elongate conductive member comprising the following steps. First and second source electromagnetic waves are caused to propagate in first and second directions, respectively, along the elongate conductive member. At least one reflected electromagnetic wave propagates along the elongate conductive member if at least one of the first and second source electromagnetic waves encounters an anomaly. The electric field of reflected electromagnetic waves is sensed. The magnetic field of reflected electromagnetic waves is sensed. A direction of propagation of reflected electromagnetic waves is determined based on the electric field of reflected electromagnetic waves and the magnetic field of reflected electromagnetic waves.

DETAILED DESCRIPTION

Figure 1:
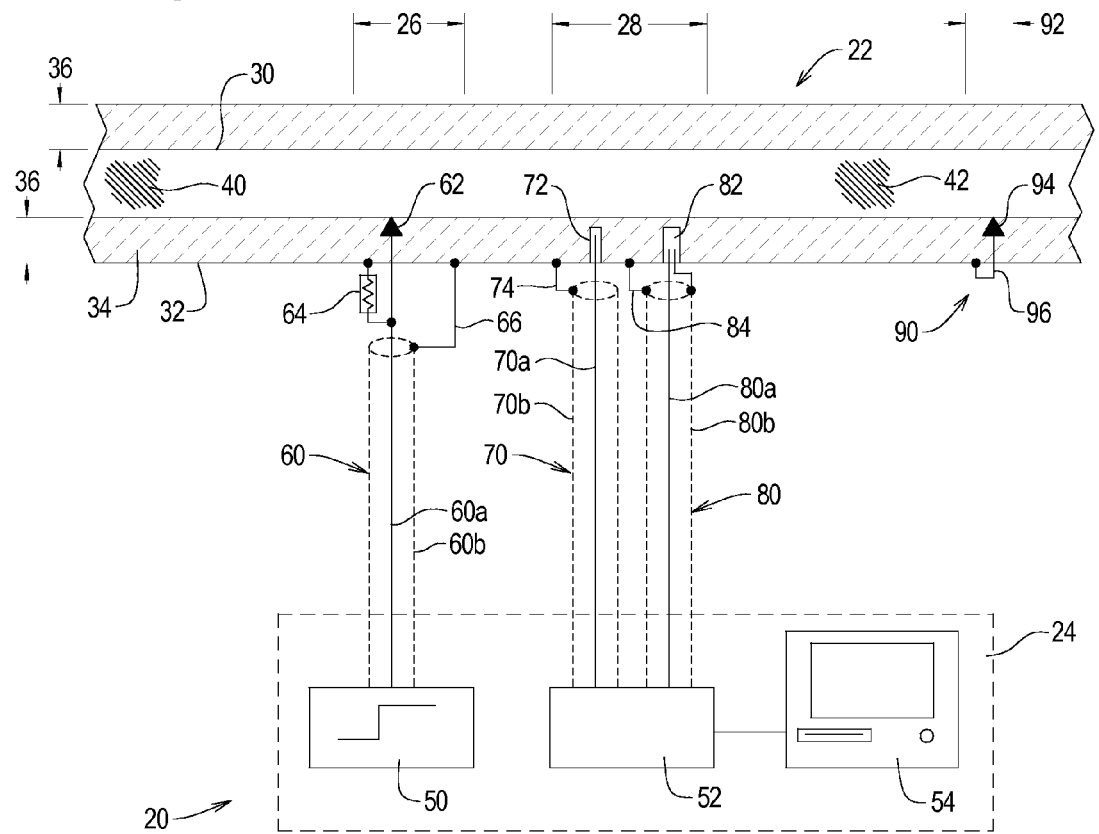
FIG. 1 is a somewhat schematic view of a typical measurement setup used to implement the principles of the present invention in the context of a pipeline system.

The present invention may be embodied as a system or method in which reflected electromagnetic waves returning from anomalies located in opposite directions on an elongate conductive member, such as a pipeline, are selectively viewed. In particular, overlapping return signals from both directions pass through the measurement point. The electric field (E) and the magnetic field (B) of signals propagating in opposite directions are measured at a single measurement location on the member. Separating the signals by direction of arrival allows determination of the distance to the anomaly or anomalies detected using an electromagnetic pipe inspection method. The systems and methods of the present invention allow inspection of complete segments of pipe over extended lengths without direct access to the surface of the pipe.

More specifically, the relationship between electric and magnetic field polarity of an electromagnetic signal is associated with direction of travel of the signal. Accordingly, the relationship between electric and magnetic field polarity of a signal passing through a given point on a conductive member suggests the direction of travel of the signal. The relationships between electric and magnetic field polarity of signals arriving from opposite directions are thus different. Accordingly, identification of the origin of a return signal may be determined based on relationships between electric and magnetic field polarity. Identification of the origin of signals passing through a given point on a conductive member allows the signals to be separated by direction of arrival. Based on this information, not only can the distance of an anomaly from the measurement point be determined, but the direction along the elongate conductive member relative to the measurement point can also be determined.

More specifically, the electric $\vec{E}$ and magnetic $\vec{B}$ field vectors are related to the Poynting vector $\vec{S}$ (which is in the direction of wave propagation) by the vector relation:

$$\vec{S} = \frac{1}{\mu}\vec{E} \times \vec{B},$$

where μ represents the magnetic permeability.

A method implementing the principles of the present invention may be embodied by separately measuring the electric and magnetic fields with field sensors and combining the output of the sensors in the proper polarity to separate the two signals passing through the measurement location from opposite directions. The combination of the sensor outputs can be done automatically using a computer or math functionality on the data acquisition system. Sensor outputs can also be combined by directly adding and subtracting the electrical sensor output signals using hardware. In this way a single sensor probe assembly can provide separate output signals for waves reaching the sensor from opposite directions without requiring a computer or other signal processing device.

The invention may thus be embodied as an improved method of inspecting the quality and integrity of elongate conductive members using the backward reflection of an electromagnetic pulse propagating along the members. As generally discussed above, the present invention applies to any conductive member but is of particular significance when applied to elongate conductive members such as pipes or pipelines, cables, wires, and the like.

One example method of the present invention measures both the electric field (E) and the magnetic field (B) and combines the resulting signals to produce separate maps showing the condition of the member upstream and downstream of the measurement point.

More generally, the invention involves propagating an electromagnetic pulse along the pipe and observing reflected electromagnetic waves from anomalies such as corrosion and other features that might affect the integrity of the system. By measuring delay or propagation time of a given signal associated with an anomaly, the distance to the anomaly from the measurement point can be determined. Based on the electric field and magnetic field of the given signal, the direction of the anomaly from the measurement point can also be determined.

The principles of the present invention may be implemented using a single sensor location on the pipe and does not employ a linear phased array of many sensors. Two separate graphical maps showing pipe condition as a function of distance to the left (first direction) and to the right (second direction) of the measurement point are automatically generated. The generation of two separate graphical maps as described herein allows each anomaly to be plotted in direction as well as distance.

It is necessary to identify the direction of arrival of a given signal to determine the location of the anomalies, such as faults, detected by the electromagnetic pipe inspection method. The electric field E and the magnetic field B can be measured at a single measurement location on the pipe using field sensors or probes. Overlapping return signals from both sides pass through the measurement point. Signals arriving from opposite directions have different electric and magnetic field polarity relationships which allow separation of signals by direction of arrival. The electric $\vec{E}$ and magnetic $\vec{B}$ field vectors are related to the Poynting vector $\vec{S}$ (which is in the direction of wave propagation) by the vector relation:

$$\vec{S} = \frac{1}{\mu}\vec{E} \times \vec{B},$$

where μ represents the magnetic permeability.

By measuring the electric and magnetic fields with field sensors and combining the sensor outputs in the proper polarity, the signals passing through the measurement location from opposite directions may be identified and separated. The signal separation is possible due to the vector nature of wave propagation, where identical waves propagating in opposite directions will have the same polarity for their electric field vectors but opposite polarity for their magnetic field vectors as indicated by the above equation.

An example anomaly detection system 20 of the present invention for detecting anomalies along a pipe system 22 will now be explained in further detail with reference to FIG. 1 of the drawing. FIG. 1 further illustrates an example measurement system 24 that may be used by the example anomaly detection system 20. The pipe system 22 defines a source or injection location 26 and the probe, sensor, or measurement location 28.

Figure 2:
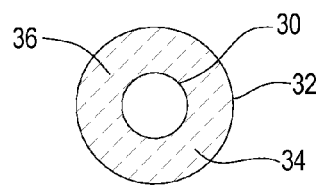
FIG. 2 is a section view taken along lines 2-2 in FIG. 1.

FIGS. 1 and 2 illustrate that the pipeline system 22 includes a metallic pipe 30 under test, an outer metallic shield (pipe shield) 32, and insulation 34 that fills a space 36 between the pipe 30 and the pipe shield 32. The insulation 34 can be air, urethane foam, or other dielectric material. The pipe 30 is typically well centered in the shield. The pipeline system 22 thus forms a constant impedance coaxial transmission line capable of propagating electromagnetic waves in the TEM mode.

FIG. 1 also depicts anomalies in the form of areas of corrosion 40 and 42 on the outside surface of the pipe 30. The areas of corrosion are located at two spaced locations along the pipe system 22 and can affect the transmission of electromagnetic waves along the pipe 30. Generally speaking, the impedance of a coaxial transmission line depends on the diameter of the inner and outer conductor and the electromagnetic properties of the material between them. In the example pipe system 22 of FIG. 1, the areas of corrosion 40 and 42 can change the diameter of the inner conductor, affecting impedance. Additionally, corrosion products such as iron oxide can spread into the space between the conductors, which also affects the impedance of a coaxial transmission line by modifying the permittivity and permeability. Changes in impedance in a coaxial transmission line cause electromagnetic pulses traveling along the coaxial transmission line to reflect back toward the location of the source of the electromagnetic pulse.

FIG. 1 further illustrates that the example measurement system 24 comprises a pulse generator 50, a signal receiver 52, and a digital computer 54. The signal receiver 52 is operatively connected to the computer 54.

A first coaxial cable 60 connects a contact 62, a terminating resistor 64, and a first connector lead 66 to the pulse generator 50. A second coaxial cable 70 connects an electric field sensor or probe 72 and a second connector lead 74 to the signal receiver 52. A third coaxial cable 80 connects a magnetic field sensor or probe 82 and a third connector lead 84 to the signal receiver 52.

The contact 62, which may be a hardened steel point, establishes a low-resistance electrical contact between a center conductor 60a of the first coaxial cable 60 and the pipe 30. The terminating resistor 64 is connected between the center conductor 60a and the pipe shield 32. The first connector lead 66 connects an outer conductor 60b of the first coaxial cable 60 to the conductive pipe shield 32. The contact 62, terminating resistor 64, and the first connector lead 66 are arranged at the injection location 26 along the pipe system 22.

The electric field sensor 72 and magnetic field sensor 82 are arranged at least partly within the insulation space 36. A center conductor 70a of the second coaxial cable 70 connects the electric field sensor 72 to the signal receiver 52. The second connector lead 74 is connected between an outer conductor 70b of the second coaxial cable 70 and the pipe shield 32. A center conductor 80a of the third coaxial cable 80 connects the magnetic field sensor 82 to the signal receiver 52. The third connector lead 84 is connected between an outer conductor 80b of the third coaxial cable 80 and the pipe shield 32. The electric field sensor 72 and magnetic field sensor 82 are arranged at the measurement location 28 along the pipe system 22.

With the connections formed as shown in FIG. 1, operation of the pulse generator 50 generates an electrical pulse that excites first and second source electromagnetic waves which propagate in both directions from the injection location 26 along the pipe system 22. In particular, the source electromagnetic waves excited by the pulse generator 50 propagate in the insulating space 36 formed by the pipe system 22.

The terminating resistor 64 is connected between the center conductor 60a and the pipe shield 32 to prevent reflected energy from traveling back toward the pulse generator 50. Without the termination formed by the terminating resistor 64, energy reflected back toward the pulse generator 50 could corrupt data collected by the measurement system 24, especially when the pulse generator 50 applies multiple pulses to the pipe system 22. The value of the matching terminating resistor 64 is chosen to terminate the first coaxial cable 60 in its characteristic impedance.

The example pulse generator 50 is capable of providing positive polarity 300 Volt step pulses with a risetime of 2 nanoseconds and a pulse width of 3 microseconds at a pulse repetition frequency of 100 pulses per second. The voltage pulses generated by the pulse generator 50 are transmitted through the first coaxial cable 60 and applied between the pipe 30 and pipe shield 32, which causes a current pulse to propagate in both directions from the injection location 26. The electromagnetic pulse propagates away from the injection location 26 in both directions in the space between the pipe 30 and the pipe shield 32 at a constant velocity v.

The electromagnetic pulse is partially reflected from each anomaly along the pipe. The reflections, or reflected electromagnetic waves, are received at the measurement location 28 by the electric field sensor 72 and magnetic field sensor 82. The distance to each of the anomalies 40 and 42 can be determined by the amount of time between generation of the source pulse by the pulse generator 50 and receipt of the reflection, or echo, pulse by the signal receiver 52, accounting if necessary for any distance between the injection location 26 and the measurement location 28.

The example anomaly detection system 20 is configured to analyze reflections, or echoes, which come from both the upstream side (left on FIG. 1) or downstream side (right on FIG. 1) of the measurement location 28 so that locations of corrosion can be identified unambiguously for inspection and/or repair. For clarity, the direction from the measurement location looking towards the upstream side will be referred to as the first direction, while the direction from the measurement location looking towards the downstream side will be referred to as the second direction.

The electric field sensor 72 uses capacitive coupling to sense reflections from the corrosion 40 and 42 and/or other anomalies on the pipe system 22, while the magnetic field sensor 82 uses inductive coupling to sense reflected electromagnetic waves from the corrosion 40 and 42 and/or other anomalies on the pipe system 22. The field sensors 72 and 82 respond with an output voltage which is proportional to the time rate of change of the local field at the location of the sensors 72 and 82, or the measurement location 28 in the system 20.

The example signal receiver 52 may be a fast multi-channel oscilloscope or digital transient signal receiver 52, such as a digital oscilloscope. The output signal from the electric field sensor 72 is coupled to one input channel of the signal receiver 52 through the second coaxial cable 70. The output signal from the magnetic field sensor 82 is coupled to a second input channel of the signal receiver 52 through the third coaxial cable 80. The example signal receiver 52 is capable of detecting the signals generated by the sensors 72 and 82 and storing these signals and/or data representing these signals. The term "storing signals" shall be used herein to refer to either storing the signal directly or storing data representative of the signal.

The signal receiver 52 thus records signals proportional to the time derivative of the electric field $\vec{E}$ and magnetic field $\vec{B}$ at the probe or measurement location. A first impulse is seen as the exciting wave passes the sensors 72 and 82. Later pulses are seen if signals reflect from variations in coaxial transmission line impedance, such as those caused by the areas of corrosion 40 and 42 on the pipe.

In the example system 20, the signals recorded on the signal receiver 52 are first numerically integrated to recover the local $\vec{E}$ and $\vec{B}$ field waveforms detected by the sensors 72 and 82 at the probe locations, or at the measurement location 28.

During measurement of the example pipe system 22, the signals or waveforms detected by the signal receiver 52 will show an initial step-like pulse coming from the pulse generator 50, followed by reflected electromagnetic wave or echoes coming from the anomalies formed by the areas of corrosion 40 and 42 on the pipe 22. In the example pipe system 22, reflected electromagnetic wave will be reflected from anomalies on both the right (area of corrosion 40) and the left (area of corrosion 42) side of the sensor 72 and 82. The example anomaly detection system 20, which uses both electric and magnetic field sensors 72 and 82, allows unlimited time windows from a single measurement location 28.

The wave impedance of the coaxial transmission line is well known to depend on the spacing of the inner and outer conductor and the dielectric properties of the insulating media separating them. A change in the conductor spacing thus causes a corresponding change in the impedance. For example, if the inner conductor diameter is increased, the spacing decreases giving a lower wave impedance which causes voltage (and thus electric field) reflection with polarity opposite to the source polarity. Conversely, if the inner conductor diameter decreases, the wave impedance is increased, resulting in a voltage wave reflection having a polarity that is the same as the source.

If the dielectric constant of foam insulation is increased by the presence of moisture or higher density foam, the local wave impedance will be lowered and a reflection with polarity opposite to the source will be generated. The duration of the reflected signal corresponds with the length over which the increased dielectric material occurs. The presence of corrosion products or other material with high dielectric constant in the space between the pipe and the outer shield will also cause a voltage reflection with polarity opposite to the source impulse waveform. Conversely, a gap in the shield or a region of missing insulation will result in higher wave impedance, and this higher wave impedance will reflect a voltage pulse with the same polarity as the source.

The electric field polarities are the same for reflected electromagnetic waves from any particular type of anomaly regardless of the direction of propagation. For the magnetic fields, however, the polarity depends on the direction of propagation. For example, the B field and E field are the same for a reflection from the area of corrosion 40 on the left side, while signals reflected from the area of corrosion 42 on the right side have B field polarity opposite to the E field polarity.

The signals may be processed directly on the signal receiver 52, or the sensor or signal data stored by the signal receiver 52 may be transmitted to the digital computer 54. If the digital computer 54 is used, the digital computer 54 performs the time integration of the sensor waveforms numerically.

The computer 54 may further scale the output levels such that the amplitudes thereof are substantially equal to the amplitude of the initial exciting pulse arriving from the pulse generator 50. Scaling the output levels compensates for any differences in sensitivity of the sensors 72 and 82.

After the signal waveforms representing the electric and magnetic fields at the measurement location 28 have been scaled, these signals may be added to obtain the wave propagating in the one direction (e.g., the first direction) and subtracted to obtain the wave propagating in an opposite direction (e.g., the second direction). This establishes the direction of propagation of reflected signals so that the absolute location of each anomaly on the pipe is now fully determined from a single measurement location 28. One waveform represents points upstream of the measurement sensors, while the other waveform with the difference signal maps the points downstream of the measurement location 28.

To calibrate the system, a marker 90 is placed at a known location 92 along the pipe system 22. The marker 90 establishes a direct short circuit connection between the pipe 30 and the pipe shield 32. The marker consists of a second electrical contact 94 (which can be a hardened steel point) and a fourth connector lead 96. The fourth connector lead 96 forms a low inductance connection between the second electrical contact 94 and the pipe shield 32. The marker 90 thus forms a high quality and consistent connection between the pipe 30 and pipe shield 32 which will forms a known "anomaly" that will reflect a predetermined quantity of energy back toward the source location 26 and measurement location 28.

The marker 90 may be used to calibrate the wave speed of propagation in the insulation 34. A wave speed of 1.07 nanoseconds per foot is typically measured for the urethane foam insulation used on the Alaska pipeline, but other pipe systems may exhibit different wave speeds. Determination of wave speed is thus used for range scale calibration. The marker 90 also allows verification of proper measurement system operation by providing a reflection the parameters of which are predetermined and thus known. The level of attenuation of the reflected pulse as a function of distance from the marker gives an overall indication of the quality of the insulation.

From the foregoing, it should be clear that the present invention may be embodied in forms other than those described above. The above-described systems are therefore to be considered in all respects illustrative and not restrictive.

What is claimed is:

1. A method of detecting an anomaly on an elongate conductive member comprising the steps of:
   causing a source electromagnetic wave to propagate along the elongate conductive member such that the source electromagnetic wave passes through the at least one anomaly, where the anomaly causes a reflected electromagnetic wave to propagate the elongate conductive member;
   configuring a first sensor to generate an electric field vector signal associated with an electric field of the reflected electromagnetic wave at a measurement location along the pipe system;
   configuring a second sensor to generate a magnetic field vector signal associated with a magnetic field of the reflected electromagnetic wave at the measurement location along the pipe system; and
   determining a direction of propagation of the reflected electromagnetic wave based on a relationship between polarities of the electric field vector signal and the magnetic field vector signal.

2. A method as recited in claim 1, in which the step of determining the direction of propagation comprises the step of linearly combining the electric field vector signal and the magnetic field vector signal with proper polarity for directional enhancement.

3. A method as recited in claim 2, in which the step of determining the direction of propagation comprises at least one of the following steps:
   adding an amplitude scaled electric field waveform of the electric field vector signal to an amplitude scaled magnetic field waveform of the magnetic field vector signal; and
   subtracting the amplitude scaled electric field waveform of the electric field vector signal from the amplitude scaled magnetic field waveform of the magnetic field vector signal.

4. A method as recited in claim 3, in which the step of determining the direction of propagation comprises the step of time integrating the electric field vector signal and the magnetic field vector signal to compensate for differentiation effects introduced by the first and second sensors.

5. A method as recited in claim 1, in which the first sensor generates the electric field vector signal by placing a resistive voltage divider in direct electrical contact with the elongate member.

6. A method as recited in claim 1, in which the first sensor and second sensors are configured to:
electrically add the electric field vector signal and the magnetic field vector signal to obtain a first direct output signal representing electromagnetic waves propagating in a first direction; and
electrically subtract one of the electric field vector signal and the magnetic field vector from the other of the electric field vector signal and the magnetic field vector signal to obtain a second direct output signal representing electromagnetic waves propagating in a second direction, where the second direction is opposite the first direction.

7. A method as recited in claim 1, further comprising the step of cancelling effects of the source electromagnetic wave to facilitate detection of the reflected electromagnetic wave.

8. A method as recited in claim 1, in which the source electromagnetic wave is introduced into the elongate conductive member at source location adjacent, where the source location is adjacent to the measurement location.

9. A method as recited in claim 1, in which the source electromagnetic wave is introduced into the elongate conductive member at the measurement location.

10. A system for detecting an anomaly on an elongate conductive member comprising:
a pulse generator for causing first and second source electromagnetic waves to propagate in first and second directions, respectively, along the elongate conductive member such that one of the first and second source electromagnetic waves passes through the at least one anomaly, where the anomaly causes a reflected electromagnetic wave to propagate along the elongate conductive member;
an electric field sensor for sensing a first signal associated with the electric field of the reflected electromagnetic wave at a measurement location;
a magnetic field sensor for sensing a second signal associated with the magnetic field of the reflected electromagnetic wave at the measurement location; where
a direction of propagation of the reflected electromagnetic wave is determined based on a relationship between polarities of the first signal and the second signal.

11. A method of determining whether anomalies are present on an elongate conductive member comprising the steps of:
causing first and second source electromagnetic waves to propagate in first and second directions, respectively, along the elongate conductive member, where at least one reflected electromagnetic wave propagates along the elongate conductive member if at least one of the first and second source electromagnetic waves encounters an anomaly;
configuring a first sensor to generate a first signal associated with the electric field of reflected electromagnetic waves;
configuring a second sensor to generate a second signal associated with the magnetic field of reflected electromagnetic waves; and
determining a direction of propagation of reflected electromagnetic waves based on a relationship between polarities of the first and second signals.

* * * * *